United States Patent
Stevenson et al.

(10) Patent No.: US 9,080,985 B2
(45) Date of Patent: Jul. 14, 2015

(54) OPTICAL SENSOR

(75) Inventors: Matthew Stevenson, Norwich (GB); John Wright, Norwich (GB)

(73) Assignee: seneye ltd (GB)

( * ) Notice: Subject to any disclaimer, the term of this patent is extended or adjusted under 35 U.S.C. 154(b) by 5 days.

(21) Appl. No.: 14/123,735

(22) PCT Filed: Jun. 6, 2012

(86) PCT No.: PCT/GB2012/051266
§ 371 (c)(1),
(2), (4) Date: Jan. 30, 2014

(87) PCT Pub. No.: WO2012/168703
PCT Pub. Date: Dec. 13, 2012

(65) Prior Publication Data
US 2014/0134052 A1    May 15, 2014

(30) Foreign Application Priority Data

Jun. 6, 2011 (GB) .................................. 1109431.5

(51) Int. Cl.
*G01N 21/78* (2006.01)
*G01N 21/84* (2006.01)
*G01N 21/85* (2006.01)
*G01N 31/22* (2006.01)

(52) U.S. Cl.
CPC ............ *G01N 21/78* (2013.01); *G01N 21/8483* (2013.01); *G01N 21/8507* (2013.01); *G01N 31/22* (2013.01)

(58) Field of Classification Search
None
See application file for complete search history.

(56) References Cited

U.S. PATENT DOCUMENTS 7,499,154 B2    3/2009    Stock et al.
2010/0135857 A1    6/2010    Hunter et al.

FOREIGN PATENT DOCUMENTS

EP    1840566 A1    10/2007
WO    WO 2012/168703    12/2012

OTHER PUBLICATIONS

International Search Report and Written Opinion for International Application No. PCT/GB2012/051266 mailed Sep. 14, 2012 in 12 pages.

*Primary Examiner* — Sam P Siefke
(74) *Attorney, Agent, or Firm* — Knobbe, Martens, Olson & Bear LLP (57) ABSTRACT

The present invention relates an optical sensor. In particular, the present invention relates to an optical sensor for detecting chemical components in a fluid.

The present invention comprises two or more sensors, each being configured to detect one or more chemicals in a fluid, or one or more properties of the fluid, and two or more light sources. Each sensor is associated with one light source, and each sensor is configured to emit or reflect light in response to light from the light source incident on the sensor. The emitted or reflected light is dependent upon the presence of a chemical or a property of the fluid. The two or more light sources and two or more sensors are arranged around a single light detector, which detects the color and/or intensity of the light being emitted or reflected by the sensor. Data from the light detector is passed to a remote processor for processing.

24 Claims, 11 Drawing Sheets

OPTICAL SENSOR

CROSS-REFERENCE TO RELATED APPLICATIONS

This application is the U.S. National Phase under 35 U.S.C. §371 of International Application No. PCT/GB2012/051266, filed Jun. 6, 2012, designating the United States and published in English on Dec. 13, 2012 as WO 2012/168703, and which claims priority to United Kingdom Application No. 1109431.5, filed Jun. 6, 2011.

FIELD OF THE INVENTION

The present invention relates an optical sensor. In particular, the present invention relates to an optical sensor for detecting chemical components in a fluid, an optical sensor for detecting the presence of a fluid, and a dip strip reading device for reading a dip strip having a plurality of chemically reactive portions configured to react to the presence of one or more chemicals in a fluid.

BACKGROUND OF THE INVENTION

Various products and techniques are available to measure chemicals in water; the cheapest way is to use either dip strips or chemical regent kits. Both these methods require time from the user and some know how. There are some reversible fixed colorimetric sensor pads that can be used permanently fixed in an aquarium but they still require a user to read and compare the colour which is hard under varying light sources, and the results can also be affected by subjective comparisons. Most people test water reactively and interpret one set of results to diagnose what has gone wrong.

Prior art on reversible $NH_3$ and pH sensors can be found in WO2007/115321 and EP1813939.

An alternative to manual tests and interpretation comes at a much higher cost and involves the use of Ion specific electrode probes (ISE). These devices are usually sold as single probes with a hardware solution attached to each sensor. These are expensive and temperamental in operation requiring frequent calibration over time. ISE probes suffer badly from drift as the electricity passing through the electrodes cause biological growth which covers and affects them. Recently optically based probes are becoming more popular in the scientific world as a replacement to ISE probes; they are usually at a higher cost but they offer greater accuracy and robustness. Examples include EP1840566.

We have therefore appreciated the need for an improved optical sensor for detecting chemicals in a fluid, such as water, that does not require a user to interpret colour changes.

SUMMARY OF THE INVENTION

The present invention therefore provides an optical sensor for detecting chemical components in a fluid, comprising: two or more light sources; two or more sensors, each sensor for sensing a chemical in a fluid, each of the sensors being arranged to receive light from a respective one of the two or more light sources, and each of the sensors being configured to emit or reflect light in response to the received light, wherein a colour and/or intensity of the light emitted or reflected from a sensor is dependent upon a presence of one or more chemicals to be detected in a fluid, and wherein the two or more sensors are configured to be exposed to, or in contact with, a fluid comprising one or more chemicals to be detected; a light detector arranged to receive the light emitted or reflected by the two or more sensors; a collimator arranged to guide light emitted by each of the two or more light sources to the respective two or more sensors, and configured to guide light emitted or reflected by each of the two or more sensors to the light detector; and a controller coupled to the two or more light sources and the light detector, the controller being configured to control the light sources and light detector such that only one light source is active at any one time.

Advantageously, the invention enables two or more chemical parameters to be monitored or detected using a single light detector. This reduces costs and the surface area of the device, since additional real estate is not required for two or more light detectors. The optical sensor is capable of detecting chemicals in a gas or in liquid.

In embodiments, the two or more sensors are supported on a removable substrate, which enables the sensors to be changed or replaced relatively easily. In embodiments, each of the two or more sensors are configured to detect one or more of pH, ammonia ($NH_3$), Oxygen, Carbon Monoxide, Humity or temperature. Although other chemicals or parameters may be possible.

In embodiments, the optical sensor further comprises a fluid sensor for detecting the presence of a fluid, the fluid sensor being arranged to receive light from a light source, and being configured to reflect light in response to the received light, wherein a colour and/or intensity of the light reflected from the fluid sensor is dependent upon the presence of a fluid, wherein the light detector is arranged to receive the light reflected by the fluid sensor, and the collimator is arranged to guide the light emitted by the light source to fluid sensor, and configured to guide the light reflected by the fluid sensor to the light detector. This enables the device to detect whether or not a fluid is present. If mounted on the side of a vessel containing water (for example an aquarium), a drop in water level would be detected as the water level drops below the level of the sensor.

In one embodiment, the fluid sensor comprises an optically transmissive material having at least one internally reflectable surface configured to reflect light when an outer portion of the internally reflectable surface is exposed to a fluid. In an alternative embodiment, the fluid sensor comprises an optically transmissive material having at least one internally reflectable surface configured to reflect light when an outer portion of the internally reflectable surface is devoid of a fluid.

In embodiments of the fluid sensor, the fluid sensor is supported on a removable substrate. This facilitates changing of the sensor for example when biological growth on the sensor degrades its performance.

In embodiments of the optical sensor, the optical sensor is housed in a housing, the housing comprising a sensor portion for housing the sensors, and the housing comprising a plurality of fluid holes in fluid communication with the sensor portion to permit fluid to enter the sensor portion from outside the housing. Preferably, the plurality of holes comprise a first hole coupleable to a pump for receiving a pumped fluid comprising a chemical to be detected, and the plurality of holes comprising a second hole coupleable to a drain outlet for outputting a pumped fluid from the sensor portion.

In such embodiments comprising a housing, the housing comprises a sealed portion for housing the light sources, light detector and controller, the sealed portion providing a substantially fluid-tight seal to prevent fluid entering the sealed portion. Preferably, a wall of the sealed portion comprises a portion of the collimator.

In embodiments, a first one of the two or more sensors and a second one of the two or more sensors are arranged about the light detector such that an axis of a forward reflected path of light from the first sensor is offset from an axis of a forward reflected path of light from the second sensor. Advantageously, this configuration reduces the amount of light emitted or reflected by a different sensor other than the desired sensor being received by the light detector.

In embodiments, the optical sensor further comprises a colour filter in an optical path between a sensor and the light detector, the filter for filtering a response of the sensor. Advantageously, this enables light of unwanted wavelengths to be filtered out, giving a greater signal-to-noise ratio.

In preferred embodiments, the light sources comprise a light emitting diode.

In embodiments, the controller is configured to receive colour and/or intensity data from the light detector. Preferably, the controller is coupleable to a processor for processing the received colour and/or intensity data to determine the presence of a chemical in a fluid.

As such, processing can be performed remote from the device, which reduces the cost and complexity of the sensor.

In preferred embodiments, the processor is remote from the controller. The processor may, for example, comprise a computer, laptop or tablet device. Alternatively, the processor is a remote server which receives and processes the data generated by the optical sensor. In such embodiments, results may be passed back to the user to give them useful information about the quality of the fluid being monitored.

In embodiments, the controller is coupleable to a processor via a wired or wireless connection.

In some embodiments, the controller is configured to store the colour and/or intensity data in memory when there is no connection to a processor. This allows the device to continue to monitor and detect chemicals in a fluid even when no processing capability is present at any one time. Preferably, the controller is configured to output the stored colour and/or intensity data when connection is with a processor is established.

In some embodiments, the controller of the optical sensor is configured to switch the two or more light sources on and off in an operation sequence to illuminate the two or more sensors. The operation sequence may be performed periodically or substantially continuously.

The present invention also provides an optical sensor for detecting the presence of a fluid, comprising: a light source; a fluid sensor arranged to receive light from the light source, and the fluid sensor being configured to reflect light in response to the received light, wherein a colour and/or intensity of the light reflected from the fluid sensor is dependent upon the presence of a fluid, and wherein the fluid sensor is configured to be exposed to a fluid to be detected; a light detector arranged to receive the light reflected by the fluid sensor; a collimator arranged to guide the light emitted by the light source to the fluid sensor, and configured to guide the light reflected by the fluid sensor to the light detector; and a controller coupled to the light source and the light detector, the controller being configured to control the light source and light detector.

In such embodiments of this optical sensor, the fluid sensor comprises an optically transmissive material having at least one internally reflectable surface configured to reflect light when an outer portion of the internally reflectable surface is exposed to a fluid. Alternatively, the fluid sensor comprises an optically transmissive material having at least one internally reflectable surface configured to reflect light when an outer portion of the internally reflectable surface is devoid of a fluid.

In embodiments of this optical sensor, the fluid sensor is supported on a removable substrate.

Furthermore, the controller of the optical sensor may be configured to operate the light source to illuminate the sensor periodically or substantially continuously.

The present invention also provides a dip strip reading device for reading a dip strip having a plurality of chemically reactive portions configured to react to the presence of one or more chemicals in a fluid, the dip strip reader comprising: a dip strip holder for retaining a dip strip to be read, the dip strip holder comprising: a dip strip holding recess portion for holding a dip strip to be read; and a plurality of locating features, each of the plurality of locating features corresponding with a reading position along the length of a dip strip; and a dip strip reader, the dip strip reader comprising: first and second light sources; a first sensor region arranged to receive light from the first light source and configured to cooperate with the dip strip holding recess to illuminate the a dip strip held in the dip strip holding recess with light from the first light source, wherein the first sensor region is arranged to receive light emitted or reflected from a dip strip held in the dip strip holding recess, wherein a colour and/or intensity of the light emitted or reflected from the dip strip held in the dip strip recess is dependent upon a presence of one or more chemicals to be detected in a fluid; a second sensor region arranged to receive light from the second light source and configured to cooperate with the plurality of locating features to illuminate one of the plurality of locating features with light from the second light source, wherein the second sensor region is arranged to receive light emitted or reflected from one of the plurality of locating features, wherein a colour and/or intensity of the light emitted or reflected from the plurality of locating features is dependent upon a presence and/or position of one of the plurality of locating features; a light detector arranged to receive light emitted or reflected from the first and second sensor regions; a collimator arranged to guide light emitted by each of the first and second light sources to the respective first and second sensor regions, and configured to guide light received from the respective first and second sensor regions to the light detector; and a controller coupled to the first and second light sources and the light detector, the controller being configured to control the light sources and light detector such that only one light source is active at one any time.

Such a device enables a dip strip to be read and compared against any number of look up tables, whilst removing the subjectivity of a user making a manual comparison by eye.

In embodiments of the dip strip reading device, the first sensor region and the second sensor region are arranged about the light detector such that an axis of a forward reflected path of light from the first sensor region is offset from an axis of a forward reflected path of light from the second sensor region.

In embodiments, the dip strip reading device further comprises a colour filter in an optical path between a sensor and the light detector, the filter for filtering a response of the sensor.

Preferably, the light sources comprise a light emitting diode.

In embodiments, the controller is configured to receive colour and/or intensity data from the light detector. Preferably, the controller is coupleable to a processor for processing the received colour and/or intensity data to determine the presence of a chemical in a fluid. In some embodiments, the controller is coupleable to a processor via a wired or wireless connection.

In embodiments, the plurality of locating features comprises a plurality of light-coloured dots, each light-coloured dot corresponding with a reading position along the length of the dip strip holding recess.

In some embodiments, the dip strip holder and dip strip reader comprising aligning features that cooperate to align the reader with the dip strip holder.

LIST OF FIGURES

We shall now describe the present invention by way of example only with reference to the accompanying figures, in which:

FIG. 18 shows a logic diagram to check if ambient light shield 10 (or 12) and Slide assembly (7 & 2) are fitted The features of the drawings are numbered as follows:
1. Light Emitting Diode (LED)
2. Sensor Area (PAD)
3. Light Detector
4. Multi Collimator
5. Collimator Shield Clear
6. Circuit Board
7. Clear Slide
8. Protective Membrane
9. Resin (heavily filled to stop light)
10. Light Shield Ambient
11. Containing Body
12. Ambient Light Shield Alternative design (for through flow)
13. Power and communications cable
14. Submersion sensor
15. Clear slide Alternative design
16. Specific wave length LED 1
17. Specific wave length LED 2
18. Optical filter
19. Alternative Sensor Area (PAD)
20. Device Suction cup
21. Device Float
22. Wireless signal
23. Gas or fluid Pump
24. Pipe In
25. Pipe out
26. Wired device (complete assembly)
27. Wireless device (complete assembly)
28. Fixing point
29. Water containing vessel
30. Water level
31. Device Fixing clip
32. Dip strip holder plate
33. Dip strip
34. Device rails
35. Dip strip line up sensors
36. Dip strip sensor pads
37. Dip strip holder recess
38. Device warning light
39. Device holder

DETAILED DESCRIPTION OF THE PREFERRED EMBODIMENTS

In brief, the present invention is able to continuously monitor chemical parameters remotely without the need for constant human interaction. For chemical sensing it is essentially an electronic eye that looks at the response of a colour responding pad under controlled lighting conditions. Parameters such as temperature or humidity can be measured optically or via an electronic component integrated into the product. All data (including colourmetric sensors pad colour) is logged and interpreted against a set of look up charts to interpret data into useful information. For the colourmetric sensor pads a large volume of digital look up colour comparison tables can be created which is needed as many chemical pads will behaviour differently depending on the other parameters. Traditionally only one colour comparison chart is printed for the user to do manual comparisons with. Furthermore, by logging the data, the present invention gathers and can interpret historical data, enabling more intelligent information results and help to be delivered to the user.

Importantly, no user calibration is required because a simple disposable slide is used with the active sensor pads fixed to it. If calibration was required it can be done before the user receives the pad, when they activate it via its unique serial number a different set comparison chart can be pulled over the internet if required. Because the system works optically very little drift occurs over the interval of each slide when in use so no recalibration is required over the interval of pads.

A further benefit of the present invention is that because it is optical it can be used to measure gasses as well as liquids in hostile or explosive environments. The present invention uses third parties colorimetric sensor pads (2) and films to measure pH, ammonia $NH_3$, oxygen $O_2$, Carbon Monoxide, Humidity and Temperature. All these technologies react to give a colour, hue, intensity or fluorescent change when stimulated by the presence of a chemical. At the heart of any optical probe is an electronic optical light detector, the accuracy and range of which is governed largely by price. In a high quality optical probe the optical detector is often the most expensive system component, therefore the more chemicals parameters you wish to sense the more optical sensors you require. Another negative effect other than cost is size, as each optical sensor (3) will require its own supporting architecture, control and components including a connection to an integrated processor.

Figure 1:
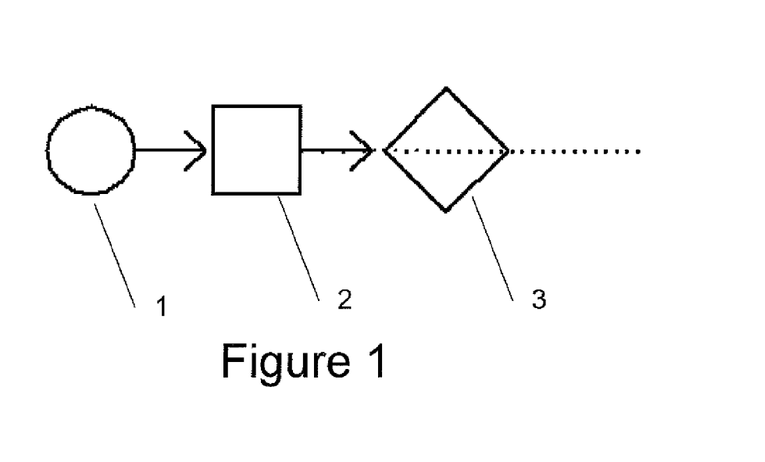
FIG. 1 shows a normal reflective sensor design(schematic top view).
Figure 2:
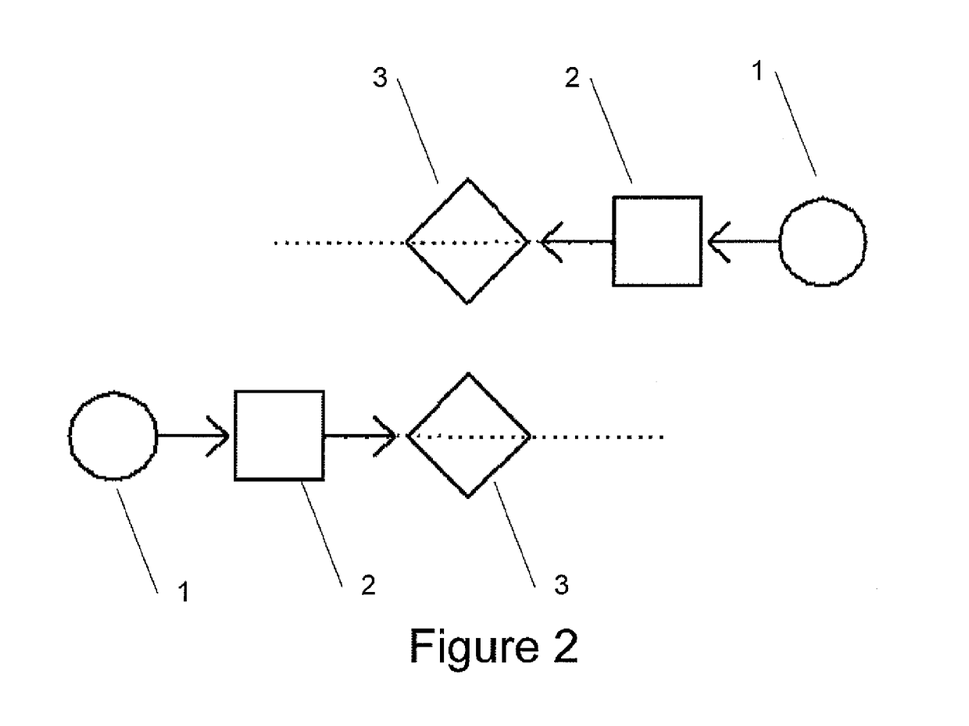
FIG. 2 shows a normal reflective sensor design with 2 sensor areas (schematic top view)
Figure 3:
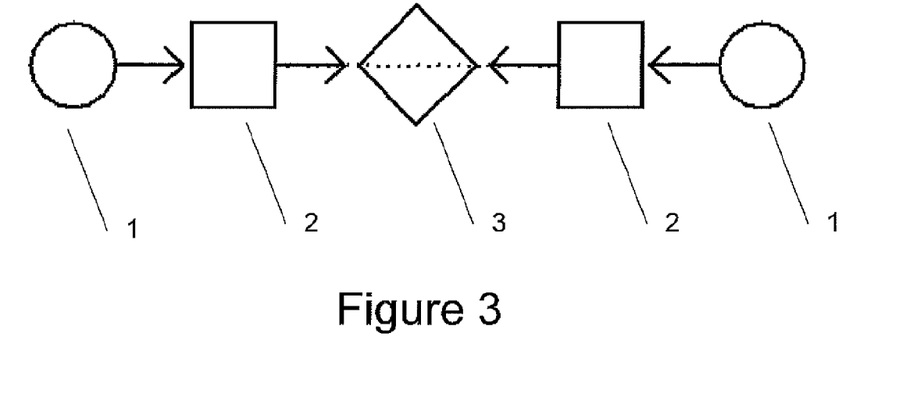
FIG. 3 shows a multiple reflective sensor design that gives high noise (schematic top view)

In traditional systems one light source and one electronic light detector is used per parameter as shown in the schematic FIG. 1, where a led (1) is arranged to shine light at a sensor area (2) and the reflected colour, hue or intensity is read by the electronic light detector (3). Normally, if another parameter is required to be read, another arrangement such as in FIG. 1 will be added as a separate optical circuit, an outline of this is shown in FIG. 2. Many more sensor areas can be added in this way. However an attempt is made to use only one optical light detector (3) as in FIG. 3 the system can result in high noise from stray light and reflections from the other pad (s).

It is therefore advantageous to on size and cost to create multi parameter sensor systems with only one light detector. To overcome this some novel methods have been explored such as mechanical wheels that turn to expose different sensor areas to the optical sensor however these have proved unreliable and inflexible as different pad can require the use of different light intensities and wavelengths.

Advantageously, the light detector of the present invention is able to measure multiple active sensing areas (2) with only one light detector (3). The invention is able to use one light detector to measure multiple parameters because of a unique collimator design.

Figure 4:
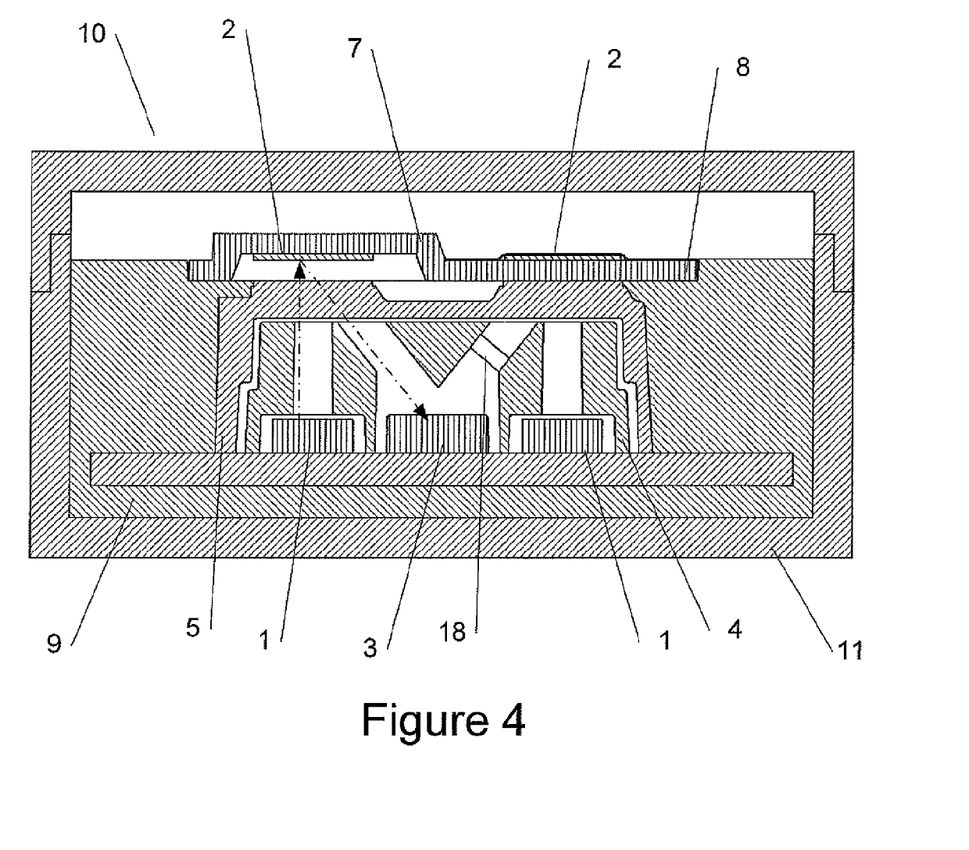
FIG. 4 shows a multiple reflective sensor design using multi collimator design (sectioned side view)
Figure 5:
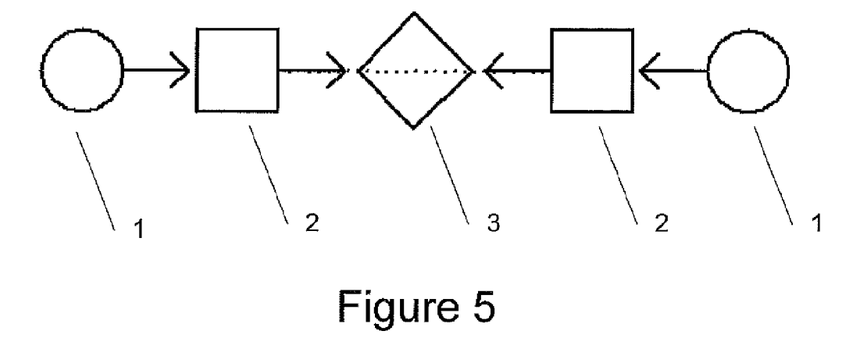
FIG. 5 shows a normal collimator arrangement 2 sensor areas (schematic top view)
Figure 6:
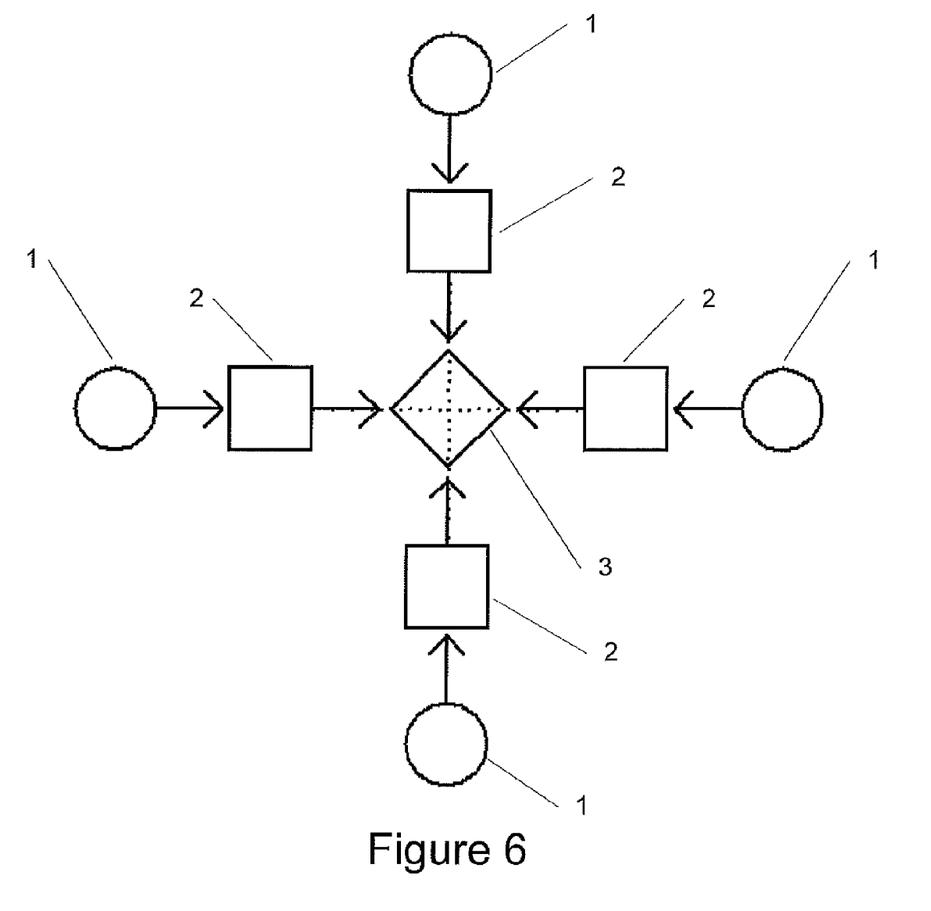
FIG. 6 shows a normal collimator arrangement 4 sensor areas (schematic top view)
Figure 7:
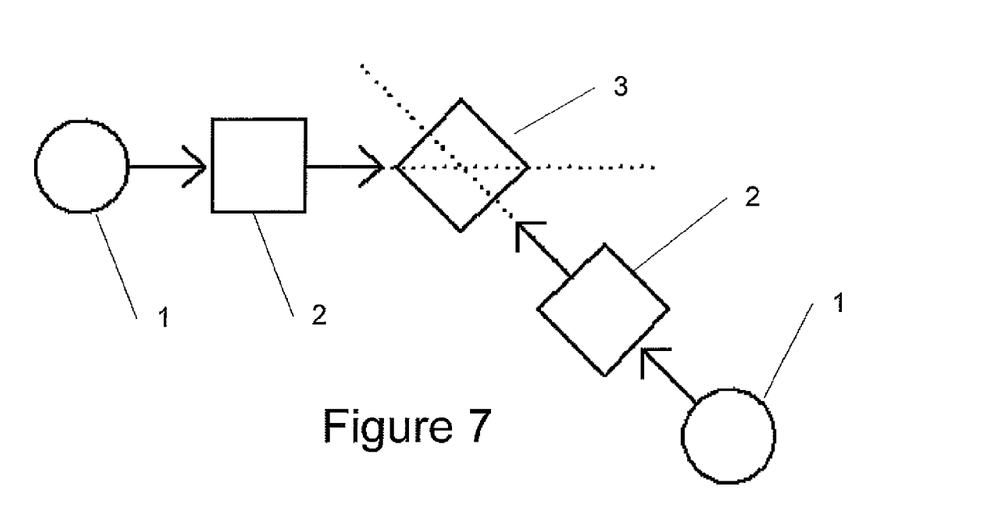
FIG. 7 shows an offset collimator arrangement 2 sensor areas (schematic top view)
Figure 8:
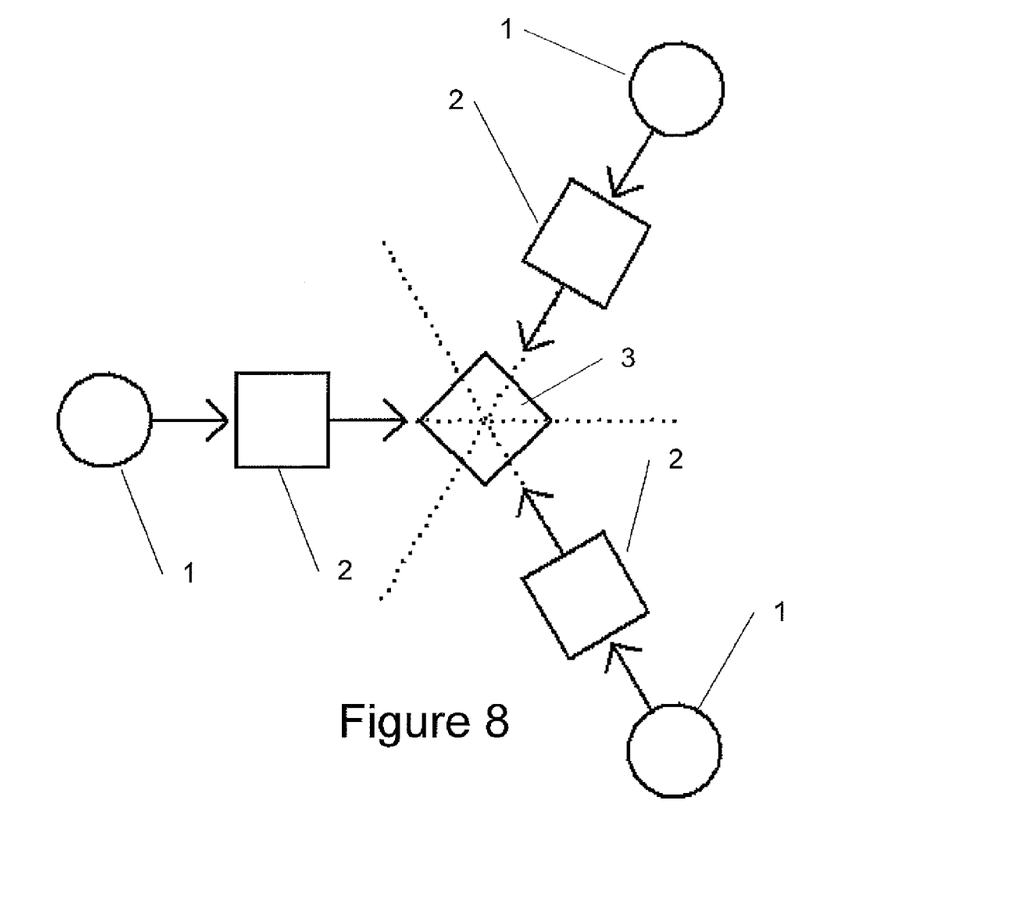
FIG. 8 shows an offset collimator arrangement 3 sensor areas (schematic top view)

In FIG. 4 a cross section shows the collimator (5) and how it is used to control and confine the light (SEE DOT/DASHED LINE) to the colourmetric sensor pad (2) and the reflected light (SEE DOT/DASHED LINE) back to the light detector (3). The design of the collimator prevents any stray light and cross over from other pads used in the arrangement. The lights (1) that are used to illuminate the sensor areas (2) are ideally able to be switched at high speed, Light emitting diodes; LED's(1) are at present the best choice. The reason for this switching is the LED's need to be controlled and switched to illuminate each sensor independently. The systems logic electronically controls the LED's so only one LED (1) can be on at any point in time and it knows which sensor area (2) is being illuminated. If this doesn't happen there would be colour cross talk from the other sensors areas (2).

Figure 9:
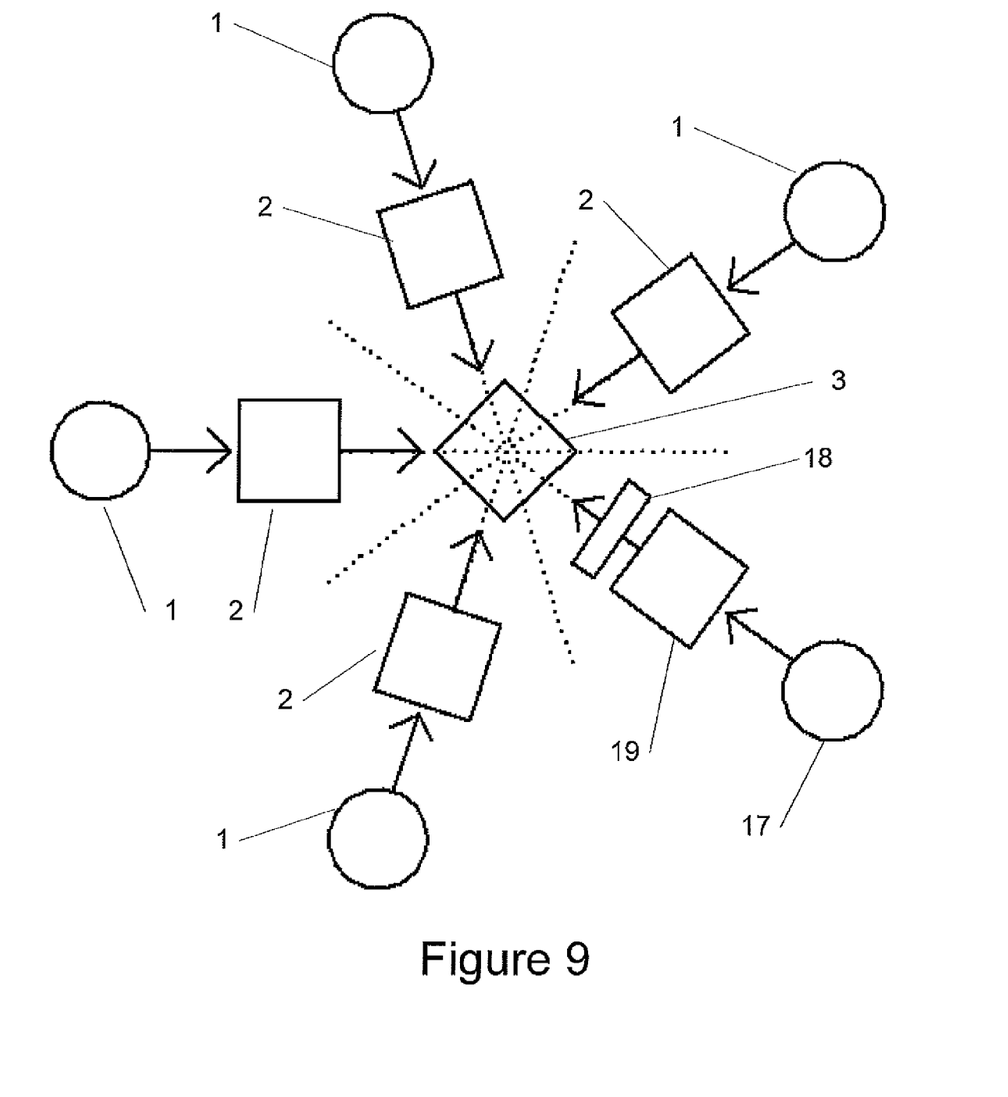
FIG. 9 shows an offset collimator arrangement 5 sensor areas (schematic top view)

With LED selection special care should be taken to select an LED which enhances the performance of the sensor area; for some this will be a high colour rendering LED with a good broad spectral output in the region where colour change is going to be seen in others it is going to be seen in the pads colour response or an LED with very narrow output to cause excitation in the case of fluorescent sensor pads. An advantage of the collimator design is that different LED's and sensor pad types can be used with different sensor areas but still using the same light detector (3), this is best shown in FIG. 9 where for example five separate sensor areas (2) (19) and three LED (1),(16) & (17) types are used. A further benefit is that a single channel can have the addition of an optical filter (18) as seen in FIG. 9.

Referring again to FIG. 4, we show a cross section side view of the collimator with (for simplicity) just two sensor areas (2) configuration, for more than two pads the layout is repeated around the light detector (3). The LED's (1) are controlled to illuminate the sensor area (2) in a known sequence. The light (SEE DOT/DASHED LINE) that is returned is read by the light detector (3). An important factor in the design is the to shield the sensor pads from all ambient light; firstly many of the chemistries used on the sensor areas (2) are not UV stable and more importantly stray light hitting the light detector (3) will cause noise and at worst overwhelm any reflected signal. In this simple section view an ambient light shield (10) is fixed in such a way as to allow water and/or gas to flow through the unit but no light to enter.

Figure 18:
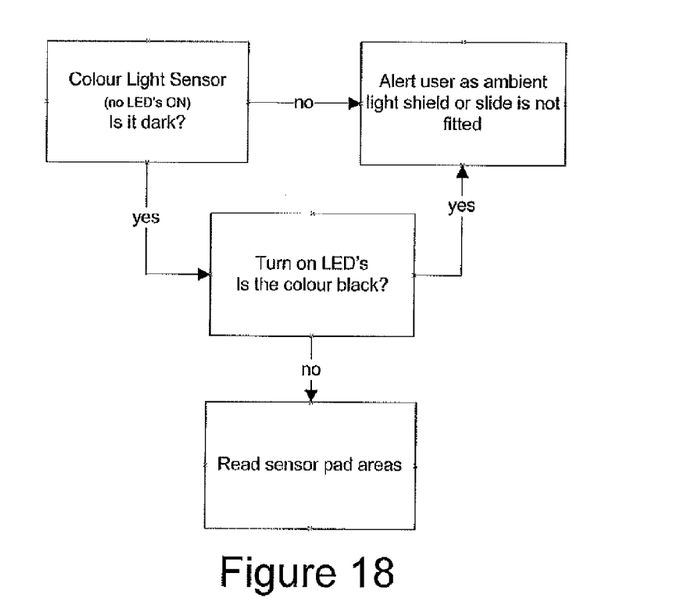

The construction of the unit is in such a way as to stop light passing through it, in this case it is achieved by a heavily filled resin (9) which also allows the device to be environmentally sealed. All the parts used to construct the collimator are covered by a specially designed clear window called the collimator shield clear (5) that allows an air cavity to be trapped once resin has been poured into the containing body (11) it is this air cavity that allows light to travel below the level of the resin and the operation of the LED's (1) and light detector (3) is not to stopped by a covering of resin (9). If the ambient light shield (10) is not present it may cause bad readings especially if the ambient light is strong or a coloured light. To ensure an ambient light shield (10) (if used in light) and slide (7) with sensor pads (2) are fitted a test procedure shown in FIG. 18 can be used. An alternative to this would be the use of various electrical sensors or electro mechanical interactions such as micro switches to show the ambient light shield was fixed; however all these options would increase cost, size and decrease reliability over the system shown in FIG. 18.

The number of sensor areas (2), LED's (1) and their arrangement around the light detector (3) can follow a number of patterns while still being governed by the laws of light and reflection. Some typical examples are outlined in FIGS. 5-9. There are two main groups of layouts: (i) a normal layout, and (ii) an offset design. The latter helps to reduce chances of stray light reaching another sensor area (2) and reflecting back causing either light noise or activating that sensor area (2) if it is fluorescent.

Figure 12:
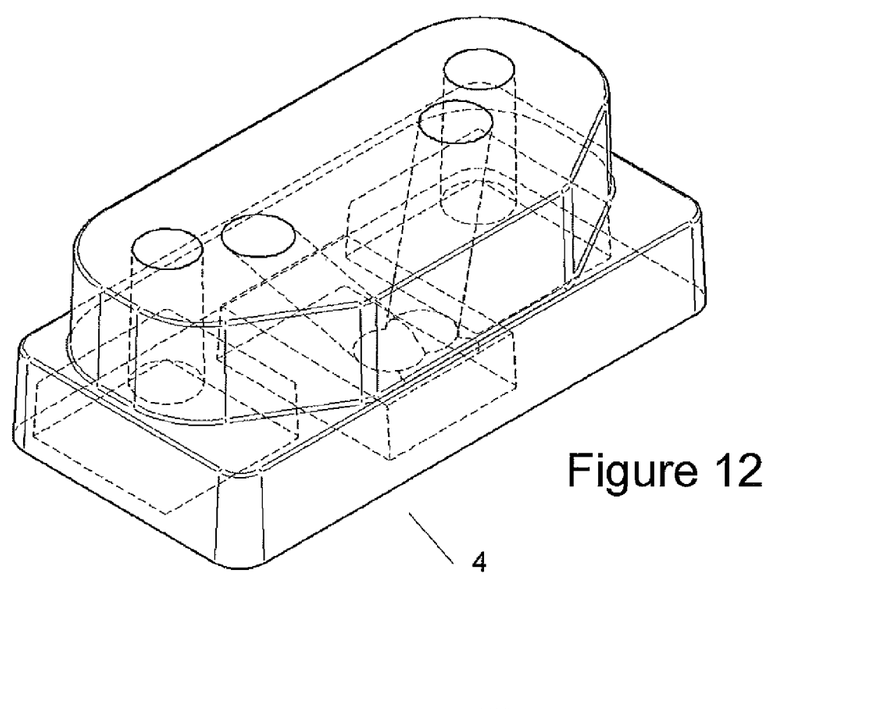
FIG. 12 shows an offset collimator device (3D with hidden detail lines)
Figure 13:
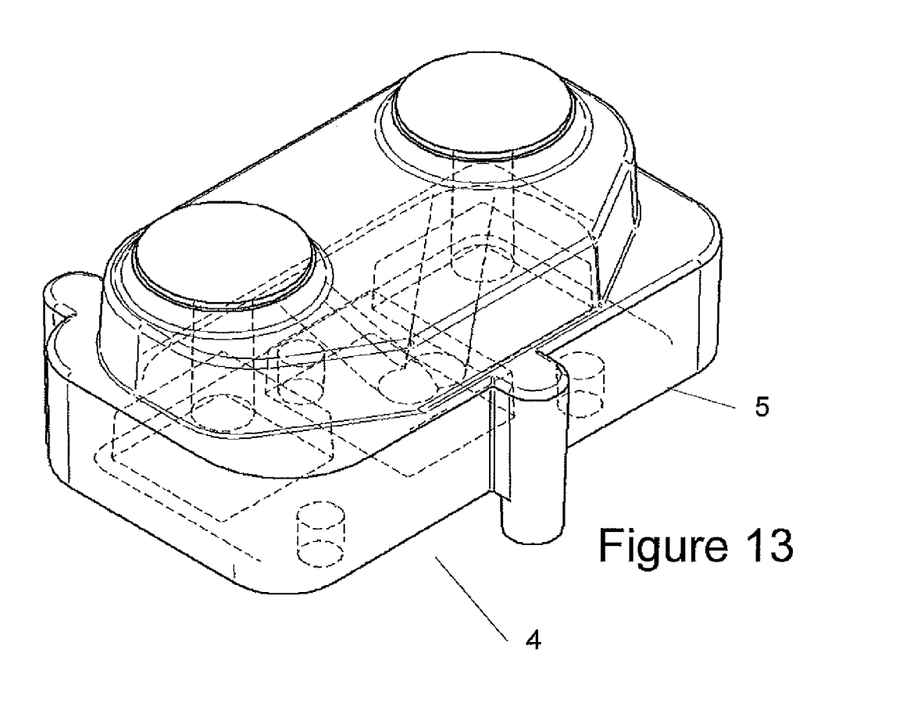
FIG. 13 shows an offset collimator device shown with clear shield (3D with hidden detail lines)

The number of sensor areas can be repeated and it is only limited by component size and the skill of the engineer in packaging; as electronics continue to miniaturise smaller devices and/or devices with more sensor areas will become increasingly easy to create. The construction of a two sensor area (2) multi collimator (4) is shown in FIG. 12 and a multi collimator (4) with collimator shield clear (5) is shown in FIG. 13.

When remotely sensing water it is useful to know that the device is submerged in water. A neat solution to achieve this is to use an optical circuit such as in FIG. 10 that can be used on the slide (7) in place of one sensor area (2) in the array. The advantage of integrating onto the slide is it also allows for it to be changed regularly and overcome any aging issues such as biofilm build up.

Figure 10:
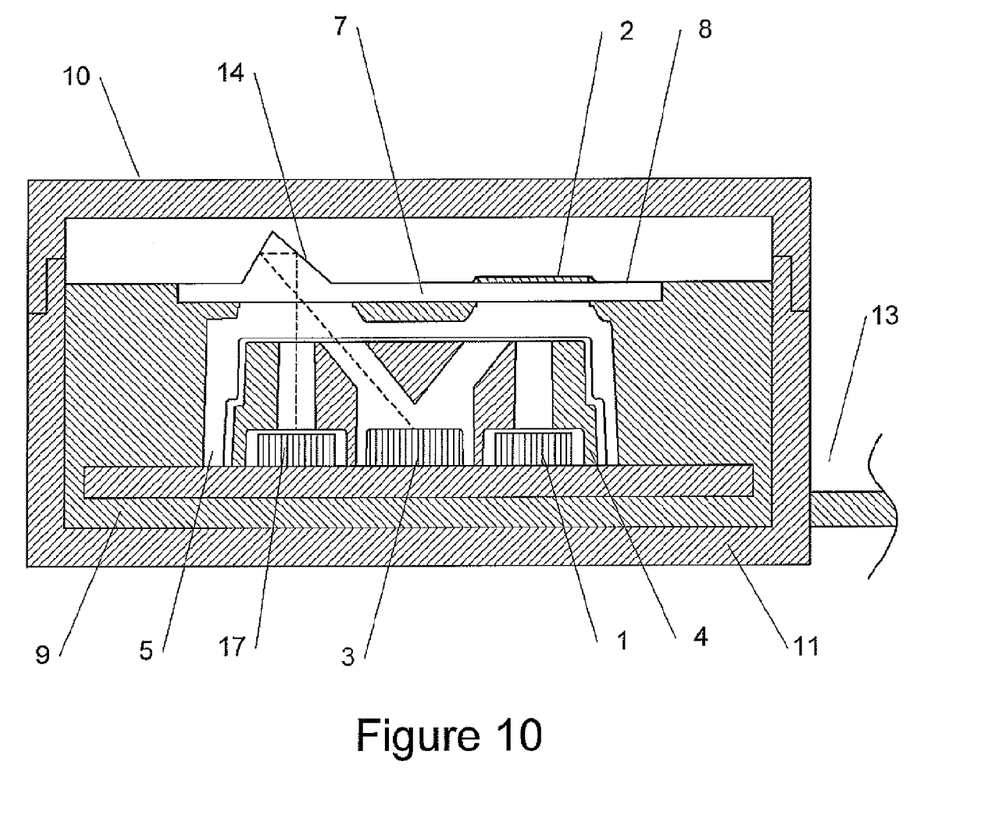
FIG. 10 shows a submersible sensor (sectioned side view)

The submersion sensor (14) works by using the refractive index of light to cause light to be reflected internally at the surface of a clear moulding when in air and back to the lights detector (3). When the submersion sensor is submerged in water light is no longer refracted internally and reflected back to the light detector (3). Any light source can be used but a known narrow angle narrow band coloured LED will create the most effective and measurable effect, this LED (17) will also require sequencing with the other LED's.

The thresholds for the reflected light on the in and out of water test can be set to allow for slight changes in surface properties over time. As an alternative the submersion detection could be designed as a using a separate colour light sensor so it can be exposed to ambient light which would be useful in some applications where an understanding of light levels against other parameters is useful if logged.

Figure 14:
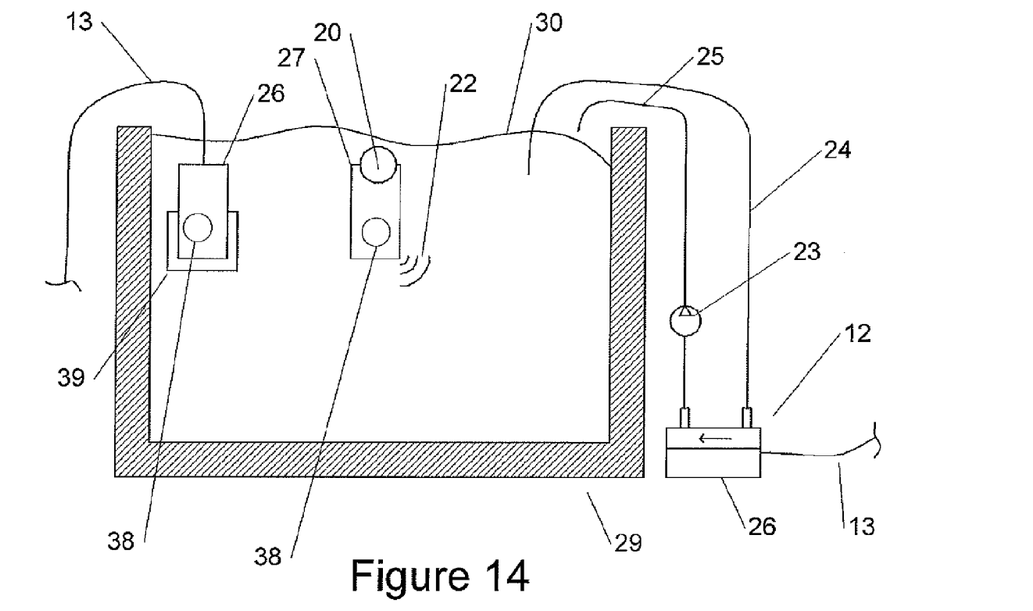
FIG. 14 shows fixing methods to allow fluid level detection (side view)
Figure 15:
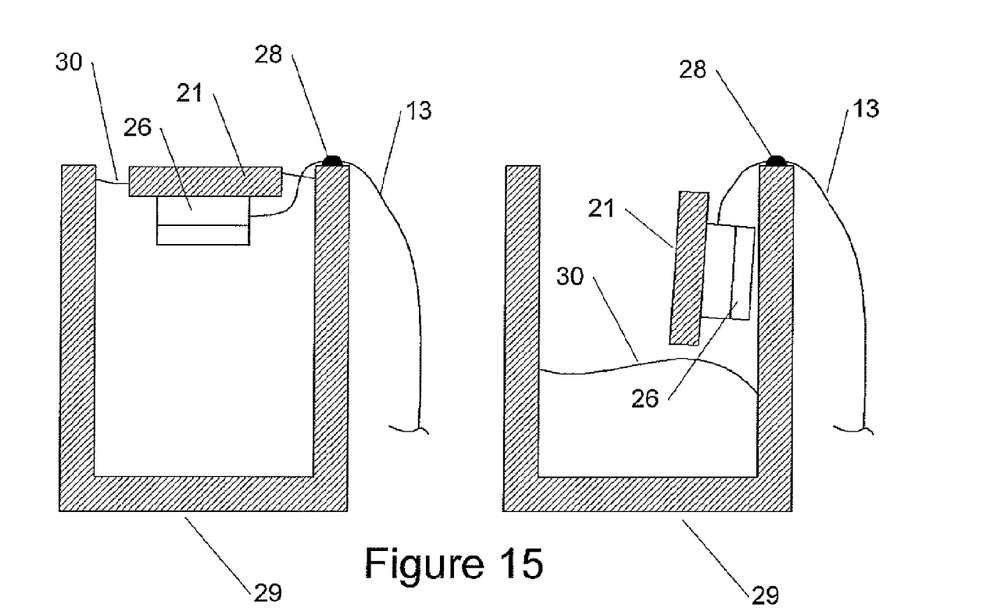
FIG. 15 shows fixing methods to allow fluid level detection using a float (side view)

The submersion sensor when fixed in fluid filled container such as the water containing vessel (29) shown in FIGS. 14 and 15 also allows the device to behave as a level meter. When a clear sided vessel is used a fixed a device holder (39) or a suction cup (20) can be used. The arrangement of the pipes (25) (24) in FIG. 14 above the water line (30) also allows for it to operate as a level meter. In environments such as lakes or fluid tanks with non-clear sides are used a device float (21) may be more appropriate so the warning lights (38) can still be seen. When using a device float (21) the devices has to be tethered via a fixing point (28) so if the level drops it is left out of water; this effect is viewable in FIG. 15.

The present invention provides an optical sensor that may monitor for the presence and/or concentration of chemicals in a fluid either periodically or continuously. The optical sensor may also be configured to monitor the presence or level of the fluid either periodically or continuously. The controller of the optical sensor is configured to switch the light sources on and off in operation cycles to illuminate the sensor areas as frequently or infrequently as required i.e. operation cycle or sequence may be configured to be repeated periodically or may run continuously, depending on the chemical(s) to be detected. Of course, the operation of such a cycle may influence on the speed at which the presence of chemicals are reported back to the user. However, the frequency of the operation cycles may be chosen dependent on at least the chemical being detected, a desired minimum detection rate etc. For example, for chemicals that are required to be detected quickly (e.g. chemicals that are detrimental to the wellbeing of the fish), the controller is configured to operate the sequence either continuously to ensure rapid detection. Since in this situation the optical sensor may be operated continuously, the detection of the chemical is therefore dependent on the reaction rate of the sensor area (2).

As the sensors areas (2) will eventually decrease in efficiency a clear substrate or slide (7) supporting the sensor area(s) (2) is used to allow fast and accurate replacement for the user. Not all sensor areas (2) are robust in application and can be prone to for example biological attack, the use of a clear slide (7) also allows some sensor areas to be mounted in reverse when needed and viewed through the clear slide (7).

The sensor areas (2) are chosen dependent on the desired chemical or property to be detected. Example sensor areas or pads include colourmetric sensor pads manufactured by Pacific Sentry LLC.

Figure 11:
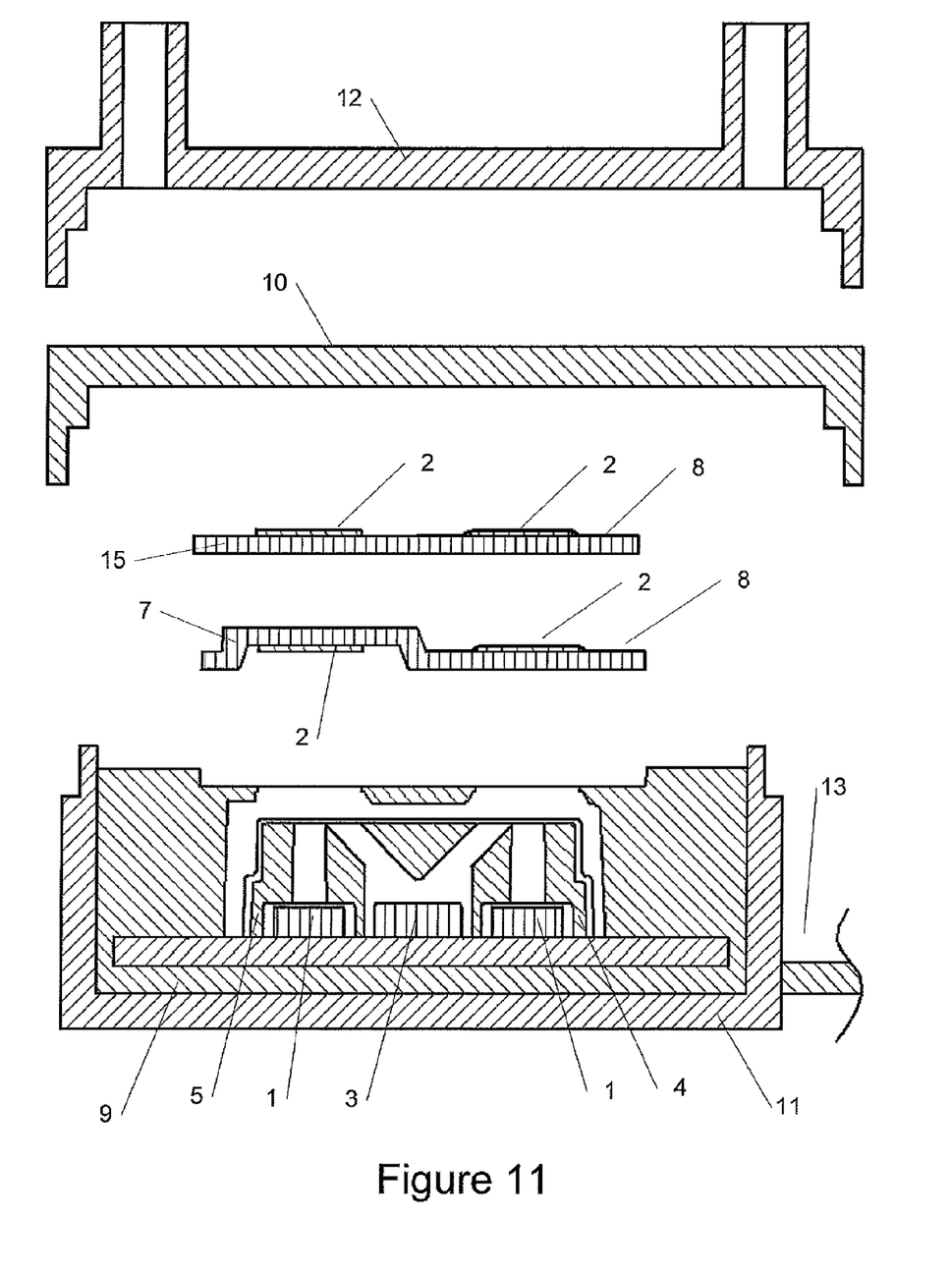
FIG. 11 shows an assembled device with optional slides and covers (exploded sectioned side view)

FIG. 11 shows two clear slide designs (7 & 15). The method used in clear slide (7 & 15) also allows a membrane (8) to be added to protect the sensor area (2) when needed. The use of a clear slide (7 & 15) also allows users to employ the same device for a variety of sensor applications by changing to different slide versions with different sensor areas (2). The clear slide (7 & 15) should also have a keying feature in its shape to allow only one orientation when fitting in the device.

In FIG. 11 the device assembly is shown as an exploded section view so we can see how a device may be constructed with a detachable clear slide (7) and a detachable ambient light shield (10). In this configuration the device can be dropped into water or used to sense air. The design of the ambient light shield (10) is designed to allow maximum gas or fluid flow but no light to enter the sensing area, this is done by creating labyrinths and baffles within the ambient light shield (10).

An alternative design of ambient light shield (12) allows gas or liquid to be pumped over the sensor areas (2). This design is explored more in FIG. 14, where it is used with two pipes (25) (24) and a pump (23) to move fluid over a device (26) through an alternative ambient light shield (12).

A variety of ways can be used to power and connect to the device to retrieve stored data for processing. In FIG. 4 the use of a wired device (26) for data and power is shown along with a wireless device (27) using battery power. When a connection to a processor is not present, data is backed up internally and synchronised when a connection is available. Alerts can be given when connections are lost between the device and the processor. The processor could be a computer or laptop connected to the device, or could be a remote server connected via the internet or any other known connection type.

Also alert levels for the parameters being monitored can be adjusted through the connection and updated locally on the device. The device is able to give warnings in a number of ways including flashing the devices warning light (38), emails, sms and internet feeds.

In most applications such as aquariums the device is used to measure parameters that change quickly or are very toxic. There are many more parameters in most applications including aquariums that will change over time but will not need recording at the same level of intervals. Some parameters require recording weekly and some monthly but again there is a need for accurate reading interpretation and storage of the readings.

Figure 16:
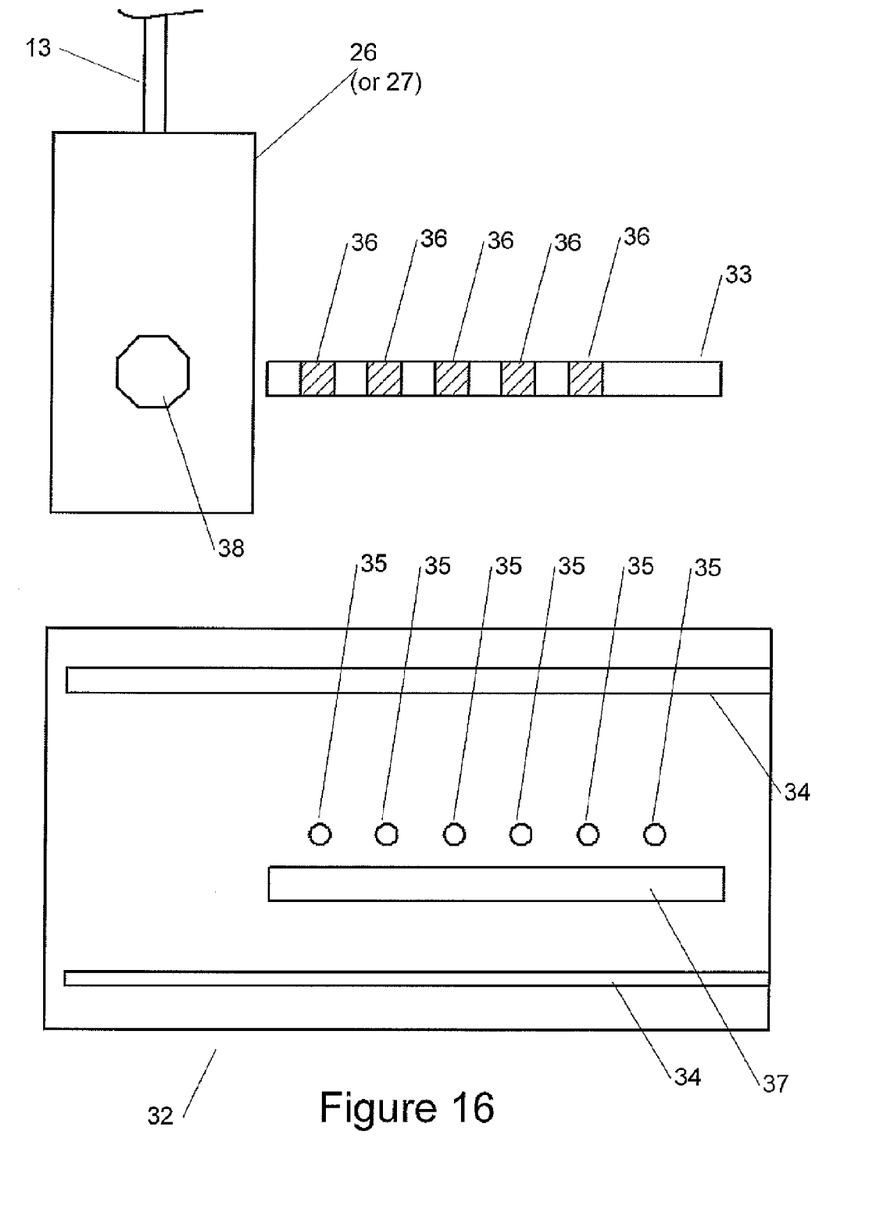
FIG. 16 shows a dip strip reader (top view)

For this reason the device has also been designed to be able to be used in conjunction with traditional dip strips (33). In FIG. 16, we show a dip strip reader (top view) with parts arranged prior to a Dip strip reading being taken. These parts consist of a wired device (26) (a wireless device (27) could also be used), a dip strip (33) with a number of dip strip sensor pads (36) affixed, in this case 6. A Dip strip holder plate (32) is also shown which consist of a dip strip holding recess (37) and a set of dip strip line up sensors (35) that are synchronised with the location of the sensor pads (36).

The dip strip line up sensors (35) are in this case a white dot on the black Dip strip holder plate (32). One collimator channel is able to see the dots whereas another is able to take the dip strip sensor pads (36) readings. Again the LED's (1) are switched during this process and the user is given feedback by the device warning light (38). The user will be informed to pause at certain intervals for readings to be taken.

An alternative approach maybe to use physical markers that the Dip strip holder plate (32) and device interact with to ensure the device is lined up over the sensors. To help the user a set of different thickness device rails (34) are built in to the Dip strip holder plate (32); this ensures correct orientation and a smooth action.

Figure 17:
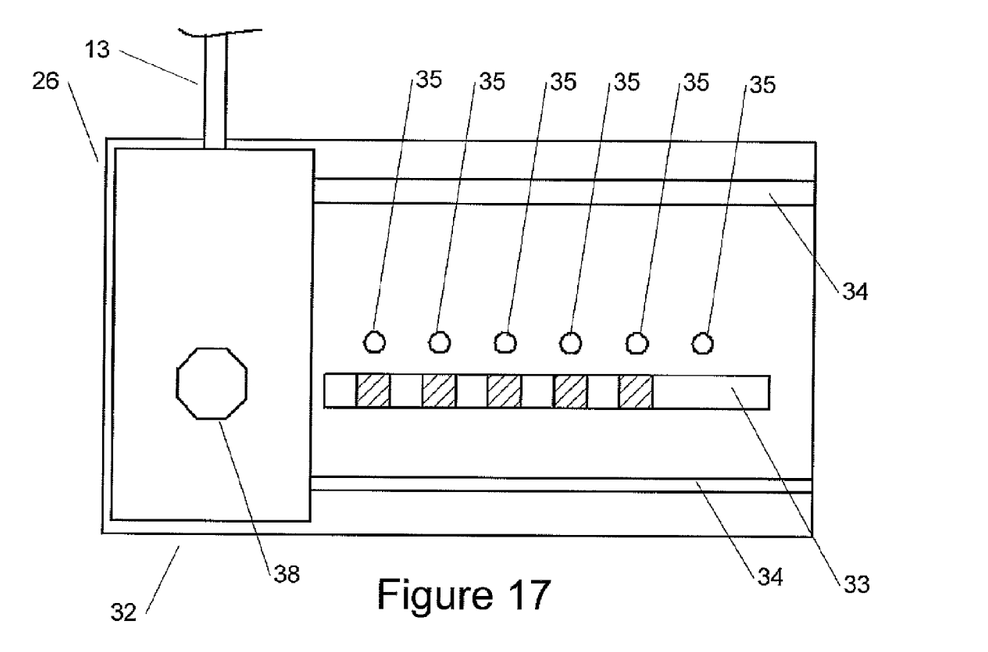
FIG. 17 shows a dip strip reader assembled (top view)

Using the device in conjunction with a dip strip (33) is simple.
1. Remove the device ambient light shield (10) and slide (7).
2. Dip the strip (33) into the fluid to be tested.
3. Place the Dip the strip (33) into the dip strip holder recess (37).
4. Place the device onto the Dip strip holder plate (32) See FIG. 17. Dip strip reader assembled (top view).
5. Move the device across the slide stopping when told to by the warning light (38) or computer.

All dip strip sensor pads (36) are read by the device, interpreted, uploaded and stored on the same database as the live data. Again multiple digital look up tables can be used. Alerts and knowledge can be passed to the user when appropriate.

Although the present invention has been described hereinabove with reference to specific embodiments, the present invention is not limited to the specific embodiments and modifications will be apparent to a skilled person in the art which lie within the scope of the present invention. Any of the embodiments described hereinabove can be used in any combination.

What is claimed is:

1. An optical sensor for detecting chemical components in a fluid, comprising:
   two or more light sources;
   two or more sensors, each sensor for sensing a chemical in a fluid, each of the sensors being arranged to receive light from a respective one of the two or more light sources, and each of the sensors being configured to emit or reflect light in response to the received light, wherein a colour and/or intensity of the light emitted or reflected from a sensor is dependent upon a presence of one or more chemicals to be detected in a fluid, and wherein the two or more sensors are configured to be in contact with a fluid comprising one or more chemicals to be detected;
a light detector arranged to receive the light emitted or reflected by each of the two or more sensors;
a collimator arranged to guide light emitted by each of the two or more light sources to the respective two or more sensors, and configured to guide light emitted or reflected by each of the two or more sensors to the light detector; and
a controller coupled to the two or more light sources and the light detector, the controller being configured to control the light sources and light detector such that only one light source is active at any one time.

2. An optical sensor according to claim 1, wherein the two or more sensors are supported on a removable substrate.

3. An optical sensor according to claim 1, wherein each of the two or more sensors are configured to detect one or more of pH, ammonia ($NH_3$), Oxygen, Carbon Monoxide, humidity or temperature.

4. An optical sensor according to claim 1, further comprising a fluid sensor for detecting the presence of a fluid, the fluid sensor being arranged to receive light from a light source, and being configured to reflect light in response to the received light, wherein a colour and/or intensity of the light reflected from the fluid sensor is dependent upon the presence of a fluid, wherein the light detector is arranged to receive the light reflected by the fluid sensor, and the collimator is arranged to guide the light emitted by the light source to fluid sensor, and configured to guide the light reflected by the fluid sensor to the light detector.

5. An optical sensor according to claim 4, wherein the fluid sensor comprises an optically transmissive material having at least one internally reflectable surface configured to reflect light when an outer portion of the internally reflectable surface is exposed to a fluid.

6. An optical sensor according to claim 4, wherein the fluid sensor comprises an optically transmissive material having at least one internally reflectable surface configured to reflect light when an outer portion of the internally reflectable surface is devoid of a fluid.

7. An optical sensor according to claim 4, wherein the fluid sensor is supported on a removable substrate.

8. An optical sensor according to claim 1, wherein the optical sensor is housed in a housing, the housing comprising a sensor portion for housing the two or more sensors, and the housing comprising a plurality of fluid holes in fluid communication with the sensor portion to permit fluid to enter the sensor portion from outside the housing.

9. An optical sensor according to claim 8, wherein the plurality of holes comprise a first hole coupleable to a pump for receiving a pumped fluid comprising a chemical to be detected, and the plurality of holes comprising a second hole coupleable to a drain outlet for outputting a pumped fluid from the sensor portion.

10. An optical sensor according to claim 8, wherein the housing comprises a sealed portion for housing the light sources, light detector and controller, the sealed portion providing a substantially fluid-tight seal to prevent fluid entering the sealed portion.

11. An optical sensor according to claim 10, wherein a wall of the sealed portion comprises a portion of the collimator.

12. An optical sensor according to claim 1, wherein a first one of the two or more sensors and a second one of the two or more sensors are arranged about the light detector such that an axis of a forward reflected path of light from the first sensor is offset from an axis of a forward reflected path of light from the second sensor.

13. An optical sensor according to claim 1, further comprising a colour filter in an optical path between a sensor and the light detector, the filter for filtering a response of the sensor.

14. An optical sensor according to claim 1, wherein the light sources comprise a light emitting diode.

15. An optical sensor according to claim 1, wherein the controller is configured to receive colour and/or intensity data from the light detector.

16. An optical sensor according to claim 15, wherein the controller is coupleable to a processor for processing the received colour and/or intensity data to determine the presence of a chemical in a fluid.

17. An optical sensor according to claim 16, wherein the processor is remote from the controller.

18. An optical sensor according to claim 17, wherein the controller is coupleable to a processor via a wired or wireless connection.

19. An optical sensor according to claim 17, wherein the processor is a remote server.

20. An optical sensor according to claim 16, wherein the controller is configured to store the colour and/or intensity data in memory when there is no connection to a processor.

21. An optical sensor according to claim 20, wherein the controller is configured to output the stored colour and/or intensity data when connection is with a processor is established.

22. An optical sensor according to claim 1, wherein the controller is configured to switch the two or more light sources on and off in an operation sequence to illuminate the two or more sensors, and wherein the operation sequence is performed periodically or substantially continuously.

23. An optical sensor for detecting the presence of a fluid, comprising:
a light source;
a fluid sensor supported on a removable substrate and arranged to receive light from the light source, and the fluid sensor being configured to reflect light in response to the received light, wherein a colour and/or intensity of the light reflected from the fluid sensor is dependent upon the presence of a fluid, and wherein the fluid sensor is configured to be exposed to a fluid to be detected;
a light detector arranged to receive the light reflected by the fluid sensor;
a collimator arranged to guide the light emitted by the light source to the fluid sensor, and configured to guide the light reflected by the fluid sensor to the light detector; and
a controller coupled to the light source and the light detector, the controller being configured to control the light source and light detector,
wherein the fluid sensor comprises an optically transmissive material having at least one internally reflectable surface configured to reflect light when an outer portion of the internally reflectable surface is exposed to a fluid or when the outer portion of the internally reflectable surface is devoid of a fluid.

24. An optical sensor according to claim 23, wherein the controller is configured to operate the light source to illuminate the sensor periodically or substantially continuously.

* * * * *